US011266613B2

(12) United States Patent
Patterson

(10) Patent No.: US 11,266,613 B2
(45) Date of Patent: Mar. 8, 2022

(54) LIDOCAINE N-OXIDE FOR USE IN THE PROPHYLAXIS OF SUDDEN CARDIAC DEATH

(71) Applicant: Biotherics Limited, Shepshed (GB)

(72) Inventor: Laurence Hylton Patterson, Shepshed (GB)

(73) Assignee: Biotherics Limited, Shepshed (GB)

( * ) Notice: Subject to any disclaimer, the term of this patent is extended or adjusted under 35 U.S.C. 154(b) by 61 days.

(21) Appl. No.: 16/756,987

(22) PCT Filed: Oct. 18, 2018

(86) PCT No.: PCT/GB2018/053012
§ 371 (c)(1),
(2) Date: Apr. 17, 2020

(87) PCT Pub. No.: WO2019/077356
PCT Pub. Date: Apr. 25, 2019

(65) Prior Publication Data
US 2021/0121421 A1  Apr. 29, 2021

(30) Foreign Application Priority Data
Oct. 18, 2017 (GB) ........................ 171714

(51) Int. Cl.
*A61K 31/167* (2006.01)
*A61P 9/06* (2006.01)
*A61K 9/00* (2006.01)
*A61K 9/08* (2006.01)
*A61K 45/06* (2006.01)

(52) U.S. Cl.
CPC ............ *A61K 31/167* (2013.01); *A61K 9/006* (2013.01); *A61K 9/007* (2013.01); *A61K 9/0019* (2013.01); *A61K 9/08* (2013.01); *A61K 45/06* (2013.01); *A61P 9/06* (2018.01)

(58) Field of Classification Search
CPC .... A61K 31/167; A61K 9/0019; A61K 9/006; A61K 9/007; A61K 9/0073; A61K 9/08; A61K 45/06; A61P 9/00; A61P 9/06
See application file for complete search history.

(56) References Cited

FOREIGN PATENT DOCUMENTS

WO       2005/044233 A1    5/2005

OTHER PUBLICATIONS

Nouri-Nigjeh, E., "Electrochemical Oxidation by Square-Wave Potential Pulses in the Imitation of Oxidative Drug Metabolism", Analytical Chemistry, vol. 83 (2011) p. 5519-5529.
Patterson, L.H., "In Vitro Metabolisn of Lignocaine to its N-oxide", J. Pharm. Pharmacol., vol. 38 (1986) p. 326.
Spear, J.F., "Effect of Lidocaine on the Ventricular Fibrillation Threshold in the Dog during Acute Ischemia and Premature Ventricular Contractions", Circulation, vol. XLVI (1972), p. 65-73.
Carden, N.L., "Lidocaine in Cardiac Resuscitation from Ventricular Fibrillation", Circulation Research, vol. IV (1956) p. 680-683.
Krzeminski, T.F., "Differential Effects of Four Xylidine Derivatives in the Model of Ischemia- and Re-perfusion-induced arrhythmias in Rats in Vivo", European Journal of Pharma., 644 (2010) p. 120-127.
PCT Search Report and Written Opinion for PCT/GB2018/053012 dated Jan. 14, 2019.
Search Report for GB1717140.6 dated Jul. 17, 2018.

*Primary Examiner* — Sarah Pihonak
(74) *Attorney, Agent, or Firm* — Katten Muchin Rosenman LLP

(57) ABSTRACT

A pharmaceutical composition comprising lidocaine N-oxide (LNO), or a pharmaceutically acceptable salt thereof, for use in a method of treatment, said method being a prophylactic treatment to prevent, or decrease the likelihood of, sudden cardiac death associated with ventricular fibrillation (VF) in a subject, whereby the composition is provided to the subject's bloodstream via the oral mucous membrane or via pulmonary absorption in the lungs or by IV administration.

20 Claims, No Drawings

LIDOCAINE N-OXIDE FOR USE IN THE PROPHYLAXIS OF SUDDEN CARDIAC DEATH

CROSS-REFERENCE TO RELATED APPLICATIONS

This application is a U.S. National Stage entry of International Application No. PCT/GB2018/053012 filed Oct. 18, 2018, which claims the benefit of GB Patent Application 1717140.6 filed Oct. 18, 2017, each of which is herein incorporated by reference in its entirety for all purposes.

The present invention relates to sudden cardiac death and specifically to prophylactic treatment regimens that can be used to prevent sudden cardiac death due to ventricular fibrillation (VF).

BACKGROUND TO THE INVENTION

Each heart beat originates as an electrical impulse from a small area of tissue in the right atrium of the heart called the sinus node or sinoatrial (SA) node. The impulse initially causes both atria to contract and then activates the atrioventricular (or AV) node which is normally the only electrical connection between the atria and the ventricles or main pumping chambers. The impulse then spreads through both ventricles via the His Purkinje fibres causing a synchronized contraction of the heart muscle.

Cardiac arrhythmia (also referred to as dysrhythmia) is a generic term for any condition in which there is abnormal heart rhythm. The heart beat (pulse) can be too fast or too slow, and can be regular or irregular.

Arrhythmia can be classified by rate (e.g., tachycardia, bradycardia), rhythm (bigeminy, fibrillation) and underlying mechanism (automaticity, re-entry).

Ventricular arrhythmias such as ventricular tachycardia (VT) and ventricular fibrillation (VF) are the major causes of sudden cardiac death. They are life-threatening cardiac rhythms commonly associated with heart attacks (acute myocardial infarctions).

Sudden cardiac death (SCD) is the single largest cause of death in the UK and other developed countries. In half of victims, death is the first symptom.

VF involves a rapid quivering of the ventricular walls that prevents them from pumping. It is characterized by an uncoordinated and potentially fatal series of very rapid and ineffective ventricular contractions, produced by multiple chaotic electric impulses. VT involves the ventricles contracting rapidly, at a rate of more than 100 times per minute. If ventricular contraction is so rapid that there is no time for the heart to refill the pulse becomes undetectable and this is known as pulseless VT. In both VF and VT there are ineffective ventricular contractions and the individual will not receive adequate blood flow to the tissues.

Since no blood is pumped from the heart, VF represents a type of cardiac arrest and, unless terminated (e.g., by defibrillation) within a few minutes of its onset, is fatal. VF is the basis of more than 70% of cases of cardiac arrest.

VF occurs in more than 70% of cases of cardiac arrest and the survival rate for this arrhythmia is still very low. Many patients survive the initial myocardial infarction but are killed by VF. If left untreated, VF can lead to death within minutes. Even for those subjects in whom a reversal to sinus rhythm is achieved, the rate of discharge from hospital is low.

According to recommendations of the American Heart Association, electric defibrillation should always be attempted as a first treatment. However, defibrillation must be carried out by trained people, and the time for defibrillation is critical, since with each minute that passes the chance of an effective reversal is reduced by 10%.

Antiarrhythmic drugs such as lidocaine, amiodarone, procainamide, and sotalol are also known and can be used for the acute treatment of hemodynamically compromising ventricular arrhythmias, such as those that occur following myocardial ischemia or infarction or during cardiac manipulative procedures such as cardiac surgery or cardiac catheterization.

For example, these may be used during cardiac arrest for treatment of refractory VF or pulseless VT.

Side effects of lidocaine include: hypotension, arrhythmias, heart block, cardiovascular collapse, bradycardia (heart rate less than 60 beats per minute) and paresthesia.

Despite the risks of fatal arrhythmia following myocardial infarction it is not recommended that any routine prophylactic antiarrhythmic drugs are used in this setting since there are not any studies which demonstrate a mortality benefit with such agents, and in fact there are some studies which show harm.

Intravenous antiarrhythmic agents such as amiodarone or lidocaine are recommended when potentially fatal arrhythmias occur. During drug infusion, constant ECG monitoring is necessary. The infusion should be terminated as soon as the basic cardiac rhythm appears to be stable, or at the earliest sign of toxicity and must be immediately stopped if there are signs of excessive cardiac depression (e.g. prolongation of PR interval and QRS complex, appearance or aggravation of arrhythmias). The PR interval is the time that extends from the beginning of the P wave (indicating the onset of atrial depolarization) until the beginning of the QRS complex (indicating the onset of ventricular depolarization).

See, for example:

AHFS Drug Information 2017. McEvoy G K, ed. Lidocaine Hydrochloride. Bethesda, Md.: American Society of Health-System Pharmacists; 2017;

Baxter Healthcare Corporation. Lidocaine hydrochloride and 5% Dextrose Injection, USP prescribing information. Deerfield, Ill.; 1998;

Ryan T J, Antman E M, Brooks N H et al. ACC/AHA guidelines for the management of patients with acute myocardial infarction: 1999 update: a report of the American College of Cardiology/American Heart Association Task Force on Practice Guidelines (Committee on Management of Acute Myocardial Infarction); and The American Heart Association. Guidelines 2005 for cardiopulmonary resuscitation and emergency cardiovascular care. Circulation. 2005; 112 (Suppl I): IV1-211.

Therefore, it is well established that lidocaine is a short-term treatment to be used in response to an emergency, life-threatening, situation. The drug is not given for any longer than necessary and is administered by an electrophysiologist (arrhythmia specialist).

A similar situation exists for amiodarone. In the UK, the use of antiarrhythmic agents for ventricular arrhythmias post myocardial infarction has been superseded by the use of Implantable Cardiac Defibrillators (ICDs) which can defibrillate these arrhythmias in high risk groups. For patients who have a large burden of arrhythmias and unpleasant shocks, amiodarone is often given as an add-on to reduce the frequency of shocks. It is only used in this very high risk situation since it produces unpleasant, and sometimes very serious, side effects (namely lung fibrosis and severe liver damage).

SUMMARY OF THE INVENTION

The present claimed invention provides a pharmaceutical composition comprising lidocaine N-oxide (LNO), or a pharmaceutically acceptable salt thereof, for use in a method of treatment, said method being a prophylactic treatment to prevent, or decrease the likelihood of, sudden cardiac death associated with ventricular fibrillation (VF) in a subject, whereby the composition is provided to the subject's bloodstream via the oral mucous membrane or via pulmonary absorption in the lungs or by IV administration.

The present invention has determined that there is a need for a prophylactic treatment regimen, to reduce the risk of sudden cardiac death due to ventricular fibrillation (VF) in patients at high risk of VF.

Patients at high risk of VF would generally fall into one of three categories: those at high risk of a myocardial infarction, those currently having a myocardial infarction, and those who have previously had a myocardial infarction.

Not only would this new treatment regimen reduce the death rate due to the prevalence of sudden cardiac death, it would also reduce the time and cost burdens on the health service that are currently associated with cardiac problems.

At present there are no routinely used antiarrhythmic agents for patients in any of these categories, other than the use of beta-blockers in the chronic phase post myocardial infarction, where ejection fraction is reduced. Beta-blockers are not particularly effective antiarrhythmic agents and are predominantly used for their beneficial effects on left ventricular remodelling and in the prevention of heart failure.

The present invention therefore provides a pharmaceutical composition comprising lidocaine N-oxide (LNO), or a pharmaceutically acceptable salt thereof, for use in a method of treatment, said method being a prophylactic treatment to prevent sudden cardiac death associated with VF in a subject, whereby the composition is provided to the subject's bloodstream via the oral mucous membrane, or via pulmonary absorption in the lungs, or by intravenous (IV) administration.

LNO is an aliphatic tertiary amine N-oxide of lidocaine, which is not new per se: it has been known in the art for a number of years. However, it has not been used previously as a prophylactic treatment for VF.

For example WO2005/044233 describes a formulation containing lidocaine N-oxide to inhibit inflammation in asthmatic lungs. The formulation can be delivered as an aerosol.

The formation of aliphatic tertiary amines as N-oxides was studied in a PhD thesis by Pamela Tien, De Montfort University, May 1999. The reductive metabolism of the N-oxides was studied and it was identified in rat tissues that LNO is reduced to lidocaine in the absence of oxygen, with no other metabolites being detected.

However, as noted above, it has been well accepted in this technical field that lidocaine is solely a short-term treatment in response to an emergency, life-threatening, situation. It is only in that life-or-death situation where the risks of causing hypotension, arrhythmia, heart block, cardiovascular collapse, and/or bradycardia are justified by the potential life-saving anti-arrhythmic effects. Lidocaine is not given for any longer than necessary because otherwise the significant risks outweigh the benefits. The side effects of lidocaine can themselves be fatal.

Studies and researches now carried out in relation to the present invention show LNO can be provided as a safe and effective prophylactic treatment, in advance of ventricular fibrillation occurring.

As noted above, until now studies have not shown any net mortality benefit with the prophylactic administration of antiarrhythmic agents, and in fact there are some studies which show harm. In other words, at best the side effects cancel out any benefits, and thus there is no overall survival rate improvement.

The present invention has determined that LNO can be provided as a prophylactic treatment, in advance of ventricular fibrillation occurring, without the detrimental effects normally associated with antiarrhythmics, e.g. the cardiotoxic effects of lidocaine. LNO has a net benefit for survival rates. Thus LNO is a safe and effective prophylactic treatment.

In this regard, when LNO is administered to the bloodstream pre-infarction, this has surprising efficacy in preventing VF occurring after an infarction does occur, and thus improving survival rates for the treated patient group, and in improving the survival rate when VF does occur.

Significantly, it does so without any signs of toxicity.

It is surprising, based on what is known for other antiarrhythmic agents, that there is a lack of off-target cardiotoxicity whist achieving good efficacy against VF, thus allowing its safe and effective use in a prophylactic setting.

Specifically, the lidocaine N-oxide can be administered with no signs of excessive reduction in contractile function, decreased heart rate, complete heart block or asystole. This has been shown when the lidocaine N-oxide is administered to the rat's bloodstream prior to an infarction (and thus prior to VF), by intravenous administration or via the oral mucous membrane.

There is no need to seek to limit the dose of the LNO, because it does not have the adverse side effects known for other antiarrhythmic agents.

For a given dose, the net overall effect on the subject's life and health, in terms of reduction of VF when weighed up against detrimental side effects, e.g. cardiotoxicity, is surprisingly good. There is a clear net benefit, making the LNO an effective and safe prophylactic, whereas what is known and understood in the art from studies for other antiarrhythmic agents is that there is either a zero net gain or even a net disadvantage to using them prophylactically.

Clearly treatment regimens that have approximately zero net gain are not used, due to cost considerations as well as health and safety considerations.

During studies on anaesthetised rats, treatment with LNO directly to the bloodstream prior to myocardial infarction could give a 100% survival rate for the rats, without there being adverse effects such as hypotension, arrhythmias, heart block, cardiovascular collapse, or bradycardia.

As noted above, there has been a long and continued need for treatments for ventricular arrhythmias such as ventricular tachycardia (VT) and VF, to reduce the instances of sudden cardiac death.

However, there has also been a long-established understanding that when antiarrhythmic agents are used prophylactically they usually do more harm than good. The CAST trial in the 1980s showed a three-fold increase in the risk of mortality with the use of flecainide in patients at high risk of VT or VF following myocardial infarction. Lidocaine therapy with lidocaine for VF or VT is a short-term treatment given solely in response to an emergency, life-threatening, situation.

Therefore there has been little further development in the field of antiarrhythmic prophylaxis since these studies. The use of antiarrhythmic prophylaxis in the context of patients at high risk for myocardial infarction, or even in patients with ongoing evolving myocardial infarction, is not supported by international guidelines including AHA and ESC.

The present invention changes that position. The present invention provides the new and useful understanding that lidocaine N-oxide can be safely and effectively provided to the bloodstream of a subject in a prophylactic manner. This can be as a post-infarction treatment, i.e. as prophylaxis against potential VF subsequent to the infarction, or can be as a prophylactic treatment regimen pre-infarction for preventing sudden cardiac death associated with VF (an application to which lidocaine is very certainly not suited).

Thus patients at high risk of VF due to being at high risk of a myocardial infarction can be provided with a prophylactic treatment regimen pre-infarction for preventing sudden cardiac death associated with VF.

Meanwhile, patients at high risk of VF due to currently having a myocardial infarction can be provided with a prophylactic treatment regimen as prophylaxis against potential VF subsequent to the infarction.

Furthermore, patients at high risk of VF due to having previously had (and survived) a myocardial infarction can be provided with a prophylactic treatment regimen before any new infarction, for preventing sudden cardiac death associated with VF.

Thus there are firstly provided prophylactic treatments for preventing sudden cardiac death associated with VF for patients who have never had an infarction, but who are at risk of myocardial infarction.

There are also secondly provided prophylactic treatments for preventing sudden cardiac death associated with VF for patients who have previously had (and survived) an infarction, who are at risk of a further myocardial infarction.

There are also thirdly provided prophylactic treatments for preventing sudden cardiac death associated with VF for patients who are currently having a myocardial infarction, to prevent VF occurring. As noted above, many patients survive an initial myocardial infarction but are killed by VF subsequent to the infarction.

The first two prophylactic treatments are regular prophylactic treatments which can be used over the mid- to long-term. They are used on an ongoing basis in the patient group, to reduce the risk of sudden cardiac death associated with VF. They may be used over a period of weeks or months or even years. They may be administered regularly, e.g. once or twice daily.

The third prophylactic treatment is a short-term prophylactic treatment. It can be used on a reactive basis in response to the infarction, to reduce the risk of sudden cardiac death associated with VF. It may be administered at the scene of an infarction occurring, and/or in an ambulance or other vehicle on-route to a hospital or other medical centre. It may be administered on one or more separate occasions. This may be on an ad hoc basis, or it may be administered over a period of hours or days.

DETAILED DESCRIPTION OF THE INVENTION

The present invention relates to a prophylactic (preventative) treatment, that is, a treatment directed to minimising, or partially or completely inhibiting, sudden cardiac death associated with VF. In one embodiment, the treatment minimises, or partially or completely inhibits, the occurrence of VF. In another embodiment, VF occurs but does not lead to sudden cardiac death.

The present invention can reduce the frequency or severity of VF. The prophylactic (preventative) treatment of the present invention does not require an absolute preclusion of VF, although in some embodiments this may be achieved. Rather, this term includes decreasing the chance of occurrence of VF and/or enhancing survival following defibrillation of VF.

Thus a method of treatment is provided, said method being a prophylactic treatment, which method comprises administration of a composition comprising LNO, or a pharmaceutically acceptable salt thereof, to a subject's bloodstream via the oral mucous membrane, or via pulmonary absorption in the lungs, or by IV, thereby preventing the occurrence of VF in the subject or reducing the severity of VF in the subject.

By preventing the occurrence of VF in the subject or reducing the severity of VF, the method serves to prevent (or decrease the likelihood of) sudden cardiac death associated with VF in the subject.

It will be appreciated that the prophylactic (preventative) treatment of the present invention does not require an absolute preclusion of sudden cardiac death associated with VF, although in some embodiments this may be achieved. Rather, this term includes decreasing the chance of sudden cardiac death associated with VF and/or improving the subject's chances of surviving VF when defibrillation and/or reperfusion therapy is used subsequent to the VF commencing.

Therefore the invention provides methods of reducing the occurrence and/or enhancing survival despite occurrence of VF in a subject, providing to a subject's bloodstream via the oral mucous membrane or by IV administration a therapeutically effective amount of a composition comprising LNO or a pharmaceutically acceptable salt thereof.

The invention further provides methods of reducing the likelihood of sudden cardiac death associated with VF in a subject, providing to a subject's bloodstream via the oral mucous membrane, via pulmonary absorption in the lungs, or by IV administration, a therapeutically effective amount of a composition comprising LNO or a pharmaceutically acceptable salt thereof.

The treatment is for minimising, or partially or completely inhibiting, sudden cardiac death associated with VF, advantageously without there being adverse effects such as one or more of hypotension, arrhythmias, heart block, cardiovascular collapse, or bradycardia. In one embodiment the treatment is for minimising, or partially or completely inhibiting, sudden cardiac death associated with VF, without there being any measurable sign of heart block or other cardiotoxicity.

The preventative treatment is suitably provided to a subject at increased risk of a heart attack.

The subject may be a mammal, in particular a human, especially an adult human.

However, it can be contemplated that the subject could be a child. It will be appreciated that human children can be at risk of VF, e.g. due to congenital heart disease.

In one embodiment, the subject is at increased risk of a heart attack due to their age. For example, the subject may be a male aged 45 or over (e.g. 50 or over, or 55 or over, or 60 or over, or 65 or over, or 70 or over), or a female aged 55 or over (e.g. 60 or over, or 65 or over, or 70 or over).

In one embodiment, the subject is at increased risk of a heart attack due to having a family history of heart attack or coronary artery disease (CAD), e.g. having a parent or sibling or grandparent who has previously had a heart attack or a diagnosis of CAD.

In one embodiment, the subject is at increased risk of a heart attack due to having high blood cholesterol, e.g. at a level of 240 mg/dl or above.

In one embodiment, the subject is at increased risk of a heart attack due to having high blood pressure, e.g. at a level of 140 over 90 or above.

In one embodiment, the subject is at increased risk of a heart attack due to presence of a longstanding autoimmune or inflammatory condition.

In one embodiment, the subject is at increased risk of a heart attack due to having been diagnosed with diabetes mellitus.

In one embodiment, the subject is at increased risk of a heart attack due to having been diagnosed with coronary artery disease (CAD).

In one embodiment, the subject is at increased risk of a heart attack due to any of the above embodiments in combination with an iatrogenic or accidental acute stress such as major surgery, or acute trauma causing blood loss.

In one embodiment, the subject is at increased risk of coronary ischaemia from other causes which may result in similar arrhythmias, e.g. coronary vasospasm (either caused by drugs, such as cocaine, or as part of coronary vasospastic disease), Kawasaki's disease, systemic hypoxia, cardiopulmonary bypass, Takayasu's arteritis and other large vessel vasculitides, aortic/coronary artery dissection, or severe aortic stenosis.

The composition comprising LNO, or a pharmaceutically acceptable salt thereof, may be administered as a regular prophylactic intervention. This in particular applies to patients who have never had an infarction, but are at risk of myocardial infarction, and also to patients who have previously had (and survived) an infarction, who are at risk of a further myocardial infarction.

Thus the composition may be administered as a regular, mid- to long-term prophylactic treatment. The composition may be used as a treatment regimen over a period of weeks, e.g. over two or more weeks, or over one month or more, or over three months or more, or over six months or more, or over a year or more. Over that time period the composition may be administered regularly, e.g. once or twice weekly or more, such as once or twice daily.

In one embodiment the composition is administered at least once a month, e.g. once or twice a week or more frequently. It may be administered once every other day, or more frequently. In one embodiment the composition is administered at least daily, such as once daily or twice daily, e.g. every morning and/or every evening.

The composition comprising LNO, or a pharmaceutically acceptable salt thereof, may however be administered as a shorter term prophylactic intervention. This in particular applies to patients who are currently having a myocardial infarction, with the prophylaxis being to prevent VF occurring subsequent to the infarction. As noted above, many patients survive an initial myocardial infarction but are killed by VF subsequent to the infarction.

Thus the composition may be administered as a short-term prophylactic treatment. The composition may be administered once or twice or more on an ad-hoc basis, e.g. at the location of the infarction and/or in an ambulance or other vehicle whilst transporting the patient with the infarction to hospital or another medical centre. The composition may be used as a treatment regimen over a period of hours, e.g. over one or two or more hours, or over six or more hours, over 12 or more hours, over 24 hours or more, over 48 hours or more, or over a week or more. Over that time period the composition may optionally be administered regularly, e.g. once or twice hourly, or once or twice daily.

The composition is administered to the subject's bloodstream via the oral mucous membrane, or via pulmonary absorption in the lungs, or by IV administration. The administration is not via the digestive system. The composition may in one embodiment be administered to the subject's bloodstream via the oral mucous membrane, or by IV administration. In one embodiment this is by IV administration, buccal administration or sub-lingual administration. However, administration via the gingival mucosa or via the palatal mucosa is also contemplated.

In one embodiment the composition is administered to the subject's bloodstream via the oral mucous membranes, e.g. by using buccal administration or sub-lingual administration.

A beneficial effect of the prophylactic regimen of the present invention is that if the subject does suffer a sudden heart attack, the subject is significantly less likely to develop VF. As discussed above, VF commonly leads to death within a few minutes of onset of symptoms, giving no time for assistance to arrive. By reducing the likelihood of VF, there is time for the subject to receive medical assistance, e.g. to get to hospital and receive reperfusion therapy, and/or to receive defibrillation treatment.

Likewise, if the subject is having a heart attack (myocardial infarction), the prophylactic regimen of the present invention can be used at that time, so that the subject is significantly less likely to develop a subsequent VF. This can therefore give time for the subject to receive medical assistance, e.g. to get to hospital and receive reperfusion therapy, and/or to receive defibrillation treatment.

Reperfusion therapy can comprise administration of drugs and/or surgery, in order to restore blood flow through or around blocked arteries. The drugs may be thrombolytics and/or fibrinolytics. The surgery may be a minimally-invasive endovascular procedure, such as a percutaneous coronary intervention (PCI) followed by a coronary angioplasty, or may be a bypass surgery that grafts arteries around blockages.

The amount of LNO, or a pharmaceutically acceptable salt thereof, provided by the composition may be 1 µM or higher, such as 5 µM or higher, e.g. 10 µM or higher or 15 µM or higher or 20 µM or higher. In one embodiment, the amount may be from 1 to 1000 µM or higher, such as from 5 to 500 µM or higher, e.g. from 10 to 300 µM or higher. It may be from 10 to 750 µM, or from 10 to 700 µM, or from 10 to 650 µM or from 10 to 600 µM. It may be from 10 to 200 µM, or from 10 to 150 µM, or from 10 to 100 µM. It may be from 20 to 200 µM, or from 20 to 150 µM, or from 20 to 100 µM. It may be from 10 to 200 µM, or from 10 to 150 µM, or from 10 to 100 µM.

LNO, or a pharmaceutically acceptable salt thereof, may be administered to the subject as a unit dose of 0.1 mg/kg or higher, such as 0.5 mg/kg or higher or 1 mg/kg or higher or 1.5 mg/kg or higher. In one embodiment, the dose may be from 0.1 to 30 mg/kg or higher, such as 0.5 to 25 mg/kg or higher or 1 to 20 mg/kg or higher or 1.5 to 15 mg/kg or higher. In one embodiment, the dose may be from 0.1 to 20 mg/kg or higher, such as 0.5 to 15 mg/kg or higher or 1 to 10 mg/kg or higher or 1.5 to 5 mg/kg or higher. It may be from 0.5 to 30 mg/kg, such as 0.5 to 25 mg/kg or 0.5 to 20 mg/kg or 0.5 to 15 mg/kg. It may be from 1 to 20 mg/kg, such as 1 to 15 mg/kg or 1 to 10 mg/kg or 1 to 5 mg/kg. It may be from 2 to 20 mg/kg, such as 2 to 15 mg/kg or 2 to 10 mg/kg or 2 to 5 mg/kg. It may be from 3 to 20 mg/kg, such as 3 to 15 mg/kg or 3 to 10 mg/kg or 3 to 5 mg/kg.

LNO, or a pharmaceutically acceptable salt thereof, may be administered to the subject as an infusion dose of 0.01 mg/kg/min or higher, such as 0.05 mg/kg/min or higher or 0.1 mg/kg/min or higher or 0.2 mg/kg/min or higher. In one embodiment, the dose may be from 0.01 to 10 mg/kg/min or higher, such as 0.05 to 5 mg/kg/min or higher or 0.1 to 2 mg/kg/min or higher or 0.2 to 1 mg/kg/min or higher. It may be from 0.1 to 10 mg/kg/min, such as 0.1 to 5 mg/kg/min or 0.1 to 2 mg/kg/min or 0.1 to 1 mg/kg/min.

The composition is administered directly to the subject's bloodstream, via the oral mucous membrane, or via pulmonary absorption in the lungs, or by IV. Therefore the active agent has direct access to the systemic circulation.

In one embodiment, the composition can be placed inside the subject's oral cavity adjacent to the cheek for buccal administration.

In another embodiment, the composition can be placed between the upper lip and gums to allow for gingival administration.

In another embodiment, the composition may be administered sublingually to a subject by placing the oral dosage form under the subject's tongue. After the composition is placed under the tongue, the subject should avoid eating, drinking, and talking in order to keep the composition in place and avoid swallowing. In one example, the subject can hold the composition under the tongue for between about 10 seconds to about 2 minutes before swallowing, e.g. for between about 15 seconds to about 1 minute.

In one embodiment, the composition may be administered by inhalation into the lungs, permitting pulmonary absorption in the lungs e.g. the composition may be in the form of an aerosol for inhalation.

WO2005/044233 describes a formulation containing lidocaine N-oxide to inhibit inflammation in asthmatic lungs, and the formulation can be delivered as an aerosol. The teachings of this document regarding the formulation of LNO as an aerosol can therefore be followed, and these teachings regarding aerosol formulations are incorporated by reference.

In one embodiment, the composition is self-administered, i.e. the subject takes the composition themselves, e.g. by buccal or sub-lingual or gingival administration, or by inhalation into their lungs. This is especially in a situation where the composition is administered to a subject who has never had an infarction, but who is at risk of myocardial infarction, or a subject who has previously had (and survived) an infarction, who is at risk of a further myocardial infarction.

In one embodiment, the composition is administered by a first aider or paramedic. This is especially in a situation where the composition is administered to a subject having a myocardial infarction, as prophylaxis against potential VF subsequent to the infarction.

In one embodiment, the composition is not administered by an electrophysiologist (arrhythmia specialist).

The present invention in one embodiment uses LNO. In another embodiment, it uses a pharmaceutically acceptable salt of LNO.

The term "pharmaceutically acceptable salt" refers to any non-toxic acid or alkaline earth metal salt of LNO. These salts can be prepared in situ during the final isolation and purification of the LNO, or by separately reacting the base or acid functions with a suitable organic or inorganic acid or base, respectively.

Representative acid salts include hydrochloride, hydrobromide, bisulfate, acetate, oxalate, valerate, oleate, palmitate, stearate, laurate, borate, benzoate, lactate, citrate, maleate and tartrate. Representative alkali metals of alkaline earth metal salts include sodium, potassium, calcium, and magnesium salts.

The composition used in the present invention suitably includes a pharmaceutically acceptable carrier.

Suitable pharmaceutical carriers are described in Remington's Pharmaceutical Sciences, A. Osol, a standard reference text in this field.

If the composition is for IV administration, it may suitably include a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4 methanol, ethers such as poly (ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

The IV administered compositions will typically contain from about 60% or more by weight of the pharmaceutical carrier, e.g. 70% or more, or 75% or more, or 80% or more, such as from 70% to 99.5% or from 75% to 95%.

The IV administered compositions will typically contain from about 0.5% to about 25% by weight of the active ingredient.

Preservatives and buffers may also be used in the IV administered compositions. In order to minimize or eliminate irritation at the site of injection, such compositions may contain a non-ionic surfactant having a hydrophilic-lipophilic balance (HLB) of from about 12 to about 17. The quantity of surfactant in such formulation preferably ranges from about 5% to about 15% by weight. The surfactant can be a single component having the above HLB or can be a mixture of two or more components having the desired HLB.

Surfactants that may suitably be used include the class of polyethylene sorbitan fatty acid esters, for example, sorbitan monooleate and the high molecular weight adducts of ethylene oxide with a hydrophobic base, formed by the condensation of propylene oxide with propylene glycol.

The IV administered compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The IV administered compositions may alternatively be in the form of a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

If the composition is for administration to the oral mucosa, it may suitably include a carrier selected from microcrystalline cellulose, silicified microcrystalline cellulose, such as ProSolv® SMCC 90 (commercially available from JRS Pharma, Patterson, N.Y., USA), dextrose, mannitol, sorbitol, maltodextrin, maltitol, and combinations thereof.

In one embodiment, the composition can comprise from about 20% to about 90% carrier by weight, e.g. about 30% to about 85%, or about 40% to about 83%, or about 50% to about 80%, or about 60% to about 80% by weight.

If the composition is for administration to the oral mucosa, it may suitably comprise a buffering agent sufficient to achieve a pH of about 7.0 to about 8.0 at the oral mucosa. In one example, the composition can achieve a pH within the oral cavity of about 7.1 to about 7.9, in another example about 7.2 to about 7.8, and in another example about 7.4 to about 7.6.

In one embodiment, the buffering agent can be any basic excipient. Non-limiting examples of buffering agents can include meglumine, glycine, sodium carbonate, calcium carbonate, sodium bicarbonate, phosphate buffer, magnesium hydroxide, and combinations thereof. In one example, the buffering agent is selected from meglumine, glycine, and combinations thereof.

To increase the passage of the LNO through the oral mucosa, one or more permeability enhancers may be used in the composition. Any permeability enhancers effective in increasing oral permeability may be used. Non-limiting examples of permeability enhancers include bile salts, surfactants, synthetic surfactants, cyclodextrins, solvents, and combinations thereof. In one example, the permeability enhancer can be sodium dodecyl sulfate, polyethylene glycol (PEG)-8 stearate (commercially available from Croda, Inc., Edison, N.J., USA), citrate buffer, oleic acid, sodium caprate, cetylpyridinium chloride, menthol, and combinations thereof. In one embodiment, the permeability enhancer can be selected from sodium caprate, cetylpyridinium chloride, and combinations thereof. In one embodiment, the permeability enhancer is sodium caprate. In one embodiment, the permeability enhancer is cetylpyridinium chloride.

In one embodiment, the composition for administration via the oral mucosa can contain about 0.1% to about 10% permeability enhancer by weight, such as from about 0.25% to about 8%, or from about 0.3% to about 6%, e.g. from about 0.5% to about 3%, or from about 0.75% to about 1.5% by weight.

In one embodiment, the composition for administration via the oral mucosa may further comprise a disintegrant, a lubricant, or other excipients as would be readily understood and used in the art.

The composition for administration via the oral mucosa can comprise a disintegrant. A disintegrant can be included to formulate a rapid disintegration of the composition following administration. Non-limiting examples of disintegrants can include crospovidone, sodium starch glycolate, crosslinked sodium carboxymethyl cellulose, low substituted hydroxypropylcellulose, guar gum, sodium alginate, and mixtures thereof. In one example, the composition can comprise from about 1% to about 20% disintegrant by weight, e.g. from about 2% to about 15%, or about 2.5% to about 10%, or about 3% to about 8%, or about 4% to about 6% by weight.

The composition for administration via the oral mucosa can comprise a lubricant. Non-limiting examples of lubricants can include sodium stearyl fumarate, magnesium stearate, calcium stearate, zinc stearate, stearic acid, glyceryl behenate, hydrogenated vegetable oils, talc, polyethylene glycol, mineral oil, and combinations thereof. In one example, the composition can comprise from about 0.05% to about 5% lubricant by weight, e.g. about 0.1% to about 3%, or about 0.25% to about 1.5%, or about 0.3% to about 1% by weight.

The composition for administration via the oral mucosa can comprise additional excipients, including, but not limited to: binders such as lactose, starch, and corn syrup; glidants such as colloidal silicon dioxide and talc; preservatives and stabilizers.

The composition for administration via the oral mucosa can also include one or more flavouring, e.g. it may comprise sweeteners, sensates, flavoring agents, salivating agents or combinations thereof.

The composition for administration via the oral mucosa can be provided in any suitable oral dosage form. Non-limiting examples of oral dosage forms can include tablets, pills, capsules, lyophilized tablets, lozenges, powders, granular substances, films and dispersible fluids. In one embodiment, the composition for buccal or sublingual administration can be provided as a tablet, pill, capsule, lyophilized tablet, or lozenge.

The foregoing invention may be better understood from the following examples, which are presented for the purposes of illustration and are not intended to limit the scope of the invention.

EXAMPLES

Example 1—Intact Anaesthetised Mice and Rats

Experiments were carried out to determine whether lidocaine N-oxide (LNO) will reduce or abolish arrhythmias which occur early after occlusion of the left coronary artery.

Stage 1:

An initial toxicity study was undertaken in pentobarbitone anaesthetized mice. A bolus dose of 100 mg/kg i.v. LNO was administered to the mice.

This dose was found to be was well tolerated.

Stage 2:

A study was carried out to assess tolerability in pentobarbitone anaesthetized rats. Two rats were infused with 60 mg/kg i.v. LNO over 20 minutes.

This dose was found to be tolerated.

The saline vehicle was assumed to have no effect, based upon data from similar controls in over 900 rats.

Stage 3:

Groups of female rats, each in the weight range of 200-300 g, were studied.

The protocol used followed that used in many previous studies seeking dose-related data for novel compounds and reference drugs.

Five minutes after the start of drug delivery the left main coronary artery was occluded (J Mol Cell Cardiol 19: 399-419 1987). This caused a region of ischaemia (verified by the occluded zone, OZ) which was maintained for the duration of the observation period (30 minutes) during which severe arrhythmias caused by the resultant cardiac ischaemia occur (J Mol Cell Cardiol 19: 399-419 1987).

This study was not randomized but was progressed from a low dose to a high dose.

Outcomes were evaluated versus a historical data base of 140 rats treated identically (0.8% saline infusion and coronary artery ligation).

Doses Tested:
3 mg/kg total dose LNO in 0.9% saline, delivered as 0.1 ml/kg/min of 1.5 mg/ml over 20 minutes.
10 mg/kg total dose LNO in 0.9% saline, delivered as 0.1 ml/kg/min of 5 mg/ml over 20 minutes.
30 mg/kg total dose of LNO in 0.9% saline, delivered as 0.1 ml/kg/min of 15 mg/ml over 20 minutes.
100 mg/kg total dose of LNO in 0.9% saline, delivered as 0.1 ml/kg/min of 50 mg/ml over 20 minutes Procedures:
From the ECG, the PR and QT and heart rate were determined.
From a femoral artery catheter, blood pressure (BP) was monitored.
Arrhythmic Score (AS) was determined by counting the number of ventricular premature beats (VPBs) and the occurrence of ventricular tachycardia (VT) and fibrillation (VF) (Cardiovasc Res 22: 656-665, 1988).
Occlusion Zone (OZ) was measured by weight (g) using a dye exclusion method (J Mol Cell Cardiol 19: 399-419 1987).

Results:

There was no evidence of off-target actions at doses of LNO up to 30 mg/kg, as indicated by heart rate and blood pressure. 10 minutes after coronary ligation the average heart rate and blood pressure were 94 mmHg and 391 beats/min respectively in the 30 mg/kg group, versus control values of 100 mmHg and 360 beats/min. The highest dose of LNO (100 mg/kg) showed evidence of off-target actions, with one death due to convulsion (a typical adverse effect of lidocaine).

Conclusion:
LNO has effective antiarrhythmic activity during regional ischaemia.
Activity is seen at doses as low as 3 mg/kg, and without off-target effects at up to 30 mg/kg i.v. This indicates a therapeutic window extending at least ten-fold from the threshold effective dose.

Example 2—Isolated Rat Heart

Model Choice:
Rat isolated heart, 30 min regional ischaemia (coronary ligation)
High baseline susceptibility to VF
Scope for detection of VF suppression by drugs
Test Solutions:
Control (saline vehicle only)
15 µM lidocaine in saline

|  | Pre-drug PR | Pre-Occl PR | Occl 5' PR | Occl 10' PR | Pre-drug BP/HR | Pre-occl BP/HR | Occl 5' BP/HR | Occl 10' BP/HR | AS | VF | VT | OZ |
|---|---|---|---|---|---|---|---|---|---|---|---|---|
| 3 mg/kg | 44 | 45 | 45 | 46 | 97/364 | 102/357 | 72/404 | 33/366 | 7 | 1 | 6 | 40 |
|  | 51 | 52 | 52 | 53 | 100/406 | 118/398 | 116/470 | 121/466 | 3 | 0 | 2 | 42 |
|  | 47 | 45 | 47 | 49 | 106/377 | 136/389 | 62/354 | 109/411 | 5 | 0 | 13 | 34 |
|  | 45 | 45 | 40 | 40 | 127/443 | 129/447 | 117/466 | 133/476 | 3 | 0 | 10 | 38 |
| Mean values | 46.75 | 46.75 | 46 | 47 | 107.5/397.5 | 121.25/423.5 | 91.75/423.5 | 99/429.5 | 4.5 | 0.25 | 7.75 | 38.5 |
| 10 mg/kg | 48 | 45 | 47 | 63 | 118/392 | 124/387 | 127/399 | 133/407 | 1 | 0 | 1 | 38 |
|  | 47 | 47 | 51 | 54 | 116/431 | 117/410 | 98/437 | 97/433 | 3 | 0 | 8 | 40 |
|  | 46 | 43 | 43 | 47 | 122/407 | 124/394 | 126/397 | 127/394 | 1 | 0 | 0 | 31 |
| Mean values | 47 | 45 | 47 | 54.67 | 118.67/410 | 121.67/397 | 117/411 | 119/411.33 | 1.67 | 0 | 3 | 36.33 |
| 30 mg/kg | 41 | 39 | 43 | 50 | 100/379 | 96/348 | 92/391 | 83/372 | 1 | 0 | 0 | 42 |
|  | 40 | 42 | 46 | 46 | 99/401 | 84/372 | 108/401 | 104/409 | 0 | 0 | 0 | 35 |
|  | 42 | 37 | 46 |  | 89/414 | 78/389 | 95/482 |  | 5 | 6 | 66 | 41 |
| Mean values | 41 | 39.33 | 45 | 48 | 96/398 | 86/369.67 | 98.33/424.67 | 93.5/390.5 | 2 | 2 | 22 | 39.33 |
| 100 mg/kg | 49 | 34 | 46 | 43 | 93/397 | 76/305 | 71/317 | 76/323 | 1 | 0 | 0 | 35 |
|  | 43 | 40 | 45 |  | 99/450 | 82/381 | 80/416 | Dead | 7 | 1 | 11 | 38 |
|  | 44 | 44 | 51 | 47 | 99/436 | 87/391 | BP lost | BP lost | 0 | 0 | 0 | 39 |
| Mean values | 45.33 | 39.33 | 47.33 | 45 | 97/427.67 | 81.67/359 |  |  | 2.67 | 0.33 | 3.67 | 37.33 |
| Mean from 140 controls |  |  |  |  | 96/374 | 100/363 |  | 100/360 | 6.1 | 0.4 | 14 | 39 |

Key:
PR = PR intervals (msec);
BP = blood pressure (mmHg);
HR = heart rate (beats/min);
AS = arrhythmia score;
VF = ventricular fibrillation (number of episodes);
VT = ventricular tachycardia (number of episodes);
OZ = occluded zone (% of total ventricular weight that was made ischaemic by coronary ligation).

Comments:

During 30 min regional ischaemia, the arrhythmia score (AS), which reflects the severity of ventricular arrhythmias, was significantly reduced by using each tested LNO dose: i.e. 3, 10, 30 and 100 mg/kg LNO. In particular it is noted that the 10 mg/kg dose group achieved a mean AS score of 1.67, as compared to the mean value from the control which was 6.1.

With a zero incidence of ventricular fibrillation episodes (VF), the 10 mg/kg dose group achieved maximal effectiveness.

150 µM lidocaine in saline
15 µM LNO in saline
150 µM LNO in saline
Method:
Randomized, blinded and fully powered trial
Groups of n=12 rat hearts
Perfusion solutions delivered via in-lines to manifold
Perfusion with test solution from 10 min before coronary ligation, and thereafter
Ischaemia-induced VF incidence recorded during 30 min ischaemia
Tissue samples taken at 30 min Results:

Both lidocaine and LNO are equally effective at reducing the incidence of VF.

The PR interval for LNO at 15 µM is substantially the same as the control. In contrast, the PR interval is higher for the 15 µM lidocaine (*) during the 30 min ischaemia.

*$p=<0.05$ vs control (2-way ANOVA and Dunnett's)

The heart rate (bpm) over the course of the trial for LNO at 15 µM is substantially the same as the control.

Conclusion:

LNO was equally as effective as lidocaine at inhibiting ischaemia-induced VF.

LNO did not show any effect on PR, whereas lidocaine did show an impact on PR.

LNO also showed only a small effect on heart rate.

Therefore, LNO is a viable pharmaceutical for use in a safe and effective prophylactic treatment for VF.

Example 3—Intact Anaesthetised Rats

Method:

Randomized, blinded and fully powered trial

Groups of n=6 anaesthetised rats

Test solutions delivered by IV to rat tail vein before induced infarction

Test Solutions:

Control (saline vehicle only)

2 mg/kg bolus lidocaine in saline 0.5 mg/kg/min infusion lidocaine in saline 2 mg/kg bolus LNO in saline 0.5 mg/kg/min infusion LNO in saline Results:

Lidocaine and LNO at 2 mg/kg bolus and at 0.5 mg/kg/min infusion are equally effective at preventing VF, with a 67% VF-free survival after 30 minutes. This compares to 0% being VF-free in the control group. LNO tests saw a longer time pass post-infarction before there was a VF event.

Conclusion

Both lidocaine and LNO were effective against VF.

However, lidocaine led to bradyarrhythmias, whereas LNO did not.

Therefore, as a safe therapeutic for preventing death, LNO worked but lidocaine did not.

Thus, LNO is a viable pharmaceutical for use in a safe and effective prophylactic treatment for VF.

An abstract entitled: "Development of OCT2013, a hypoxia-activated prodrug of lidocaine, for the treatment of ischaemia-induced ventricular fibrillation" by L. M. Hesketh et al, in the Proceedings of the British Pharmacological Society: http://www.pA2online.org/abstracts/Vol18Issue1abst169P.pdf includes graphs showing the effectiveness of "OCT2013". The chemical nature of OCT2013 was not disclosed, because that was confidential information belonging to the present applicant, but it can be confirmed that OCT2013 is LNO.

The abstract sets out that "Lidocaine and OCT2013 were equi-effective at inhibiting VF, whether administered before (FIG. 2A) or after ischaemia onset (FIG. 2B) in Langendorff preparation. OCT2013 didn't induce dose-limiting bradycardia or PR interval elongation, in contrast with lidocaine (FIG. 1A, 1B). Coronary ligation in vivo revealed similar antiarrhythmic effectiveness of OCT2013 and lidocaine via Kaplan Meier analysis (FIG. 3A)."

The abstract concludes that "OCT2013 inhibited ischaemia-induced VF in Langendorff and in vivo rat models of AMI, and was as effective as lidocaine. Unlike lidocaine, however, its effects were not limited by adverse effects on cardiac output, PR interval or heart rate."

Summary of Experimental Evidence:

Surprisingly, LNO has been found to be effective against ventricular fibrillation but without the adverse effects on cardiac output, PR interval or heart rate seen with lidocaine. Thus, LNO is a viable pharmaceutical for use in a safe and effective prophylactic treatment for sudden cardiac death associated with ventricular fibrillation.

The invention claimed is:

1. A method of treatment, said method being a prophylactic treatment to prevent, or decrease the likelihood of, sudden cardiac death associated with ventricular fibrillation (VF) in a subject, said method comprising:

administering a pharmaceutical composition comprising lidocaine N-oxide (LNO), or a pharmaceutically acceptable salt thereof, to a subject, wherein the subject is at increased risk of a heart attack, whereby the composition is provided to the subject's bloodstream via the oral mucous membrane or via pulmonary absorption in the lungs or by IV administration.

2. The method of treatment according to claim 1, wherein the treatment minimises, or partially or completely inhibits, the occurrence of VF.

3. The method of treatment according to claim 1, wherein VF occurs but does not lead to sudden cardiac death.

4. The method of treatment according to claim 3, wherein defibrillation and/or reperfusion therapy is used subsequent to the VF commencing.

5. The method of treatment according to claim 1, wherein the treatment decreases the chance of occurrence of VF and/or reduces the severity of VF.

6. The method of treatment according to claim 1, wherein the subject is a mammal.

7. The method of treatment according to claim 6, wherein the subject is an adult human.

8. The method of treatment according to claim 1, wherein the subject is at increased risk of a heart attack due to their age.

9. The method of treatment according to claim 1, wherein the subject is at increased risk of a heart attack due to having a family history of heart attack or coronary artery disease.

10. The method of treatment according to claim 1, wherein the subject is at increased risk of a heart attack due to having high blood cholesterol.

11. The method of treatment according to claim 1, wherein the subject is at increased risk of a heart attack due to having high blood pressure.

12. The method of treatment according to claim 1, wherein the subject is at increased risk of a heart attack due to having been diagnosed with coronary artery disease.

13. The method of treatment according to claim 1, wherein the composition is administered as a regular prophylactic treatment.

14. The method of treatment according to claim 13, wherein the composition is administered at least once a month.

15. The method of treatment according to claim 14, wherein the composition is administered at least once a week.

16. The method of treatment according to claim 15, wherein the composition is administered at least daily.

17. A method of treatment, said method being a prophylactic treatment to prevent, or decrease the likelihood of, sudden cardiac death associated with ventricular fibrillation (VF) in a subject, said method comprising:

administering a pharmaceutical composition comprising lidocaine N-oxide (LNO), or a pharmaceutically acceptable salt thereof, to a subject having a myocardial infarction, as prophylaxis against potential VF subsequent to the infarction, whereby the composition is provided to the subject's bloodstream via the oral mucous membrane or via pulmonary absorption in the lungs or by IV administration.

18. The method of treatment according to claim 1, wherein the composition is administered to the subject's bloodstream by IV administration, buccal administration or sub-lingual administration.

19. The method of treatment according to claim 1, wherein after administration of the composition the subject does not show signs of decreased heart rate, complete heart block or asystole.

20. A method of treatment, said method being a prophylactic treatment to prevent, or decrease the likelihood of, sudden cardiac death associated with ventricular fibrillation (VF) in a subject, said method comprising:

administering a pharmaceutical composition comprising lidocaine N-oxide (LNO), or a pharmaceutically acceptable salt thereof, to a subject, wherein the composition is administered to the subject's blood stream by IV administration, buccal administration or sub-lingual administration.

\* \* \* \* \*